United States Patent
Mahishi et al.

(10) Patent No.: US 6,756,222 B2
(45) Date of Patent: Jun. 29, 2004

(54) *ESCHERICHIA COLI* HAVING ACCESSION NO. PTA 1579 AND ITS USE TO PRODUCE POLYHYDROXYBUTYRATE

(75) Inventors: L. H. Mahishi, Maharashtra (IN); G. Tripathi, Maharashtra (IN); T. V. N. Ramchander, Maharashtra (IN); Shuban Kishen Rawal, Maharashtra (IN)

(73) Assignee: Council of Scientific & Industrial Research, New Delhi (IN)

( * ) Notice: Subject to any disclaimer, the term of this patent is extended or adjusted under 35 U.S.C. 154(b) by 14 days.

(21) Appl. No.: 09/772,304

(22) Filed: Jan. 29, 2001

(65) Prior Publication Data

US 2002/0146785 A1 Oct. 10, 2002

(51) Int. Cl.[7] .......................... C12N 1/20; C12N 15/00; C12N 1/06; C12P 7/00; C07H 2/04
(52) U.S. Cl. ................... 435/252.3; 435/71.1; 435/243; 435/252.8; 435/252.33; 435/320.1; 435/132; 536/23.2
(58) Field of Search .............................. 435/252.3, 71.1, 435/243, 252.8, 252.33, 320.1, 132; 536/23.2

(56) References Cited

U.S. PATENT DOCUMENTS 5,512,456 A * 4/1996 Dennis ...................... 435/69.1

OTHER PUBLICATIONS

Liu et al. A novel genetically engineered pathway for synthesis of poly(hydroxyalkanoic acids) in *Escherichia coli*. Applied & Environmental Microbiology. vol. 66, No. 2, pp. 739–743. 2000.*

* cited by examiner

*Primary Examiner*—Ponnathapu Achutamurthy
*Assistant Examiner*—Yong D Pak
(74) *Attorney, Agent, or Firm*—Baker Botts LLP

(57) ABSTRACT

The present invention provides a novel genetically modified *Escherichia coli* JM109 bearing accession number PTA 1579, containing the gene coding for poly-beta-hydroxybutyrate synthesis and a method of using this bacterium to produce poly-beta-hydroxybutyrate to the extent of 60% or more of the cell weight.

8 Claims, 13 Drawing Sheets

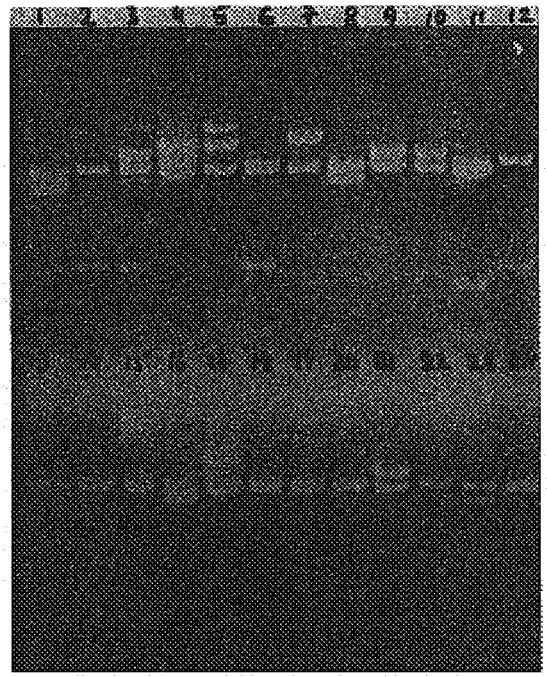
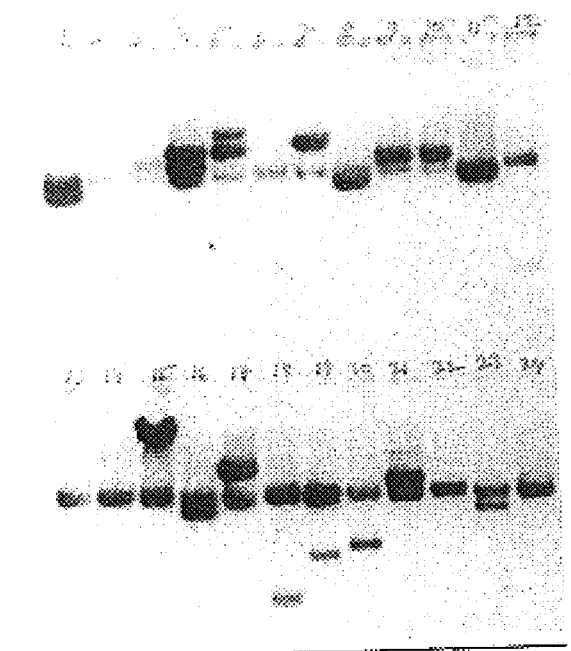
FIG.2

Fig. 8 Sa240 DNA sequence (4,826 bp)

```
GATCGGCGGCCGGTCGGCGGTGCTGGCCGCGGTGACCCTGGGGGCGCTGGCCGCTCCGGCGGTGCTGCT
GCGCCGGGGCTGGCGGCCACCGCGGAGGCGCTGGCGGCGCTGGCCCTGGTGCTGACGCTGCTGGACGT
GTACGCGGTCCACGCGGTTGGCCGCGCCGGACACCGACGGACTCGGCTTCACGGCCCTCGCGTCGGCGGT
GCTCGCGGCGCTGTGGACGGCGTACGGGCTGGCGCTGGGCAAGCTGCGCCTGCCGTTGCCGGCCGCCGT
GGTGCTGGGCCCAGTGGCCGCTGCTGTTCTGGGCCTGGGCCGTGGGCGCACCGGCGCCGGTGGTCGGGTGG
GCGCTGCTGGCCACCGCGGTGCTGGACGGGGCGATCGCCCTGTGGGGCAAGGGCGCCGGGGTGCGGGTC
ACGGCGTGCGTCGGTGGAGCGGTGATGGGCTTCTCGGCCCTGATGGTGGGCCTGGCGCTGTCCCTGACGG
CCCCGGGGCCGCTCGGGGCGGTGGCTCCGGGCGTGCTGCTGCTGACGGCCTCGGCGGCGGCCGTGGCCG
GGGCGTGGCGCGCGCCGAAGGGTTTCGCGCGGACGGGTGGTGCGGTGGCGGGGCTCGCGGCGGTGGCGG
CCGTCGGCGGCGTACCGGCGGCGGCGCTCCCGGCGGGCTGGCGGGTGCTCGCGTACCTGCTGTGCGGTCT
CGCGTTGACGGCGGTCGTCCGTTCCCGGCTGCCGGGCCACGCCGCGCGCGGGGTACTGGCGGCGTCGGG
GGCGGTGGTGGCCGGCGCGCTGGTGTGGGCGCTGCCGCCGCTCGCGGCGGTGCTGCTGGGGCCGGTGAC
GGTGCTGTCGGACGTGTGGGCGGGGACGCCCGGACGGCTTCCGGTCCGCGCTGGGGTCGACGCTGCCCTG
GTCGGAGCTGGCCGCGCGGCCCCGGTGGTGCTCGCGCTGGTGGCCGGGCATGCTGGGGGCGAGCGTAACCG
GAGGTGGCCGTCGGTCGTCCGGCTCCGGCGCCGTTGGCCGGTCCTTCTGGCTCGACGCCGGCCCCCCGGC
AGCACCGGCAGCGGGAGCCCCGGGCACGGATGCGCCGGGCGCGGCCGGGGGCGCTGCGCCGTGGCCCG
GCTGGTCCGGCTGGTCCGGCCGGCCCGGTGCGGGGGCCGGTGGTCGCGGGCGGCCTTCCGCGGCGACGC
TGCGCGGGGTCGTCGGCGCGGGCGCGGTGGCGCTCGGCTGGGGGGCCCTCCTGCTGGCCGGCGCGCTGC
TGGACGTGCCCCACGCGCTCGCGCTGGCCGGGGAGACGGCTCTGGTGGGCGTCCTGCTCGCCCTGGCGGT
CCGGGGTGGCGGCGCCGAGCGGGGCGCGACGGCGATGCCGGTGACCGCTCTGGTGGCTTCGGTGGCCGG
GGCGGTGAGCGCCGGGCTGCTGTCGCTGGCGTCCGAGGGGGCCTCGTACGCGGTGTTCGGCGCGCTGGC
GGCGCTGTTCGCCGGGGCCGCTCTGCGGGCGGGCGCCGGGGTGCCGCGTGCGGTGTTCGCGGTCGCCGC
GGTGGTCTGGGGCACCGTGATCACGGGGTTGGCGGGGCCGGTCCCTGGGGCTCGCCCCCGCACGAGGCCGC
CCCGCTGATGCTGCTGGTGCCGGCGCTGACGGTGCTGCTCGGGGCACGACTGCGGCGGAACCCGGTGGC
CTTGCCCGTGGAGCTGACGGGAGCGCTGGGCGCGCTCGTCGCCGTGGGGCTCGCGGTGTCCGACGCGCC
GTTCCTGGCCCTGGTGCTGGCGCTGTGCGGGGTGCTGGCGGCGGGGACGGCGGTGCGGCCGGAGCGGCG
GCCGGTGGCGGGCTACCTGGCGGCGACGCTGTTCGTGCTGGCCACGTGGGTGCGGCTGGCGGCCTCGGA
GGTGTCGTTCCCGGAGGCGTACACGCTGCCGGTGACGGTGCCCGCGCTGCTGGTCGGTGCGGCGCGGCG
GCGCCGGGACCCGGAGGCCTCGTCGTGGACGGCGTACGGGCCGGGGCTCGCGGCGACGCTGCTGCCCAG
CCTGGCGGTCGCCTGGACCGACCCGGACTGGCTCAGGCCGTTGCTGCTGGGGACGGCGGCGCTGGTGATC
ACCCTGCTCGGCGCGCGCCACCGGCTCCAGGCGCTGCTGCTGCTCGGCGGGACGGTGCTGGCACTGGTCG
GCCTGCACGAGCTGGCGCCGTACGTGGTGCAGGTCGCGGGTGCGCTCCCCGCTGGCTCCCGCCCGCCT
GGCCGGGCTGTTGTTGCTGGTGGTCGGGAGCGACGTGCTGGAGCAGCGGCTGCGGGACGCCCGCCGTCTGAA
GGACGCGCTGGGGCGGATGCGGTGAGCCGTGCCCGGTCCGGGGGCGCGCAGGTCACGGCGTCCCCGGGC
CGGGCGCCAGTGGCGTGGGCAACGCAGAGGGCCCGGCCCTCTGTCCGGGTGGGCGATACTGGGTTCGAA
CCAGTGACCTCTTCGGTGTGAACGAAGCGCTCTCCCACTGAGCTAATCGCCCGGGCGCACCGCAAACATT
ACCCCATGTCAGCGGTGCTCCCGGACCGTCCCCGGGCTACTCGCTGATCTTCCACGGCATGGTGAGCCCG
AACTTCCAGACGTAGATCCCGGCCAGCACCGCCATGATCACGAGCCCGAGCGTGGTGAGGATGATGTTG
CGCCGCCGGACCTTGGGATCGAGGGCCCGCTGCGCCGCTTCGGTGACCTTGCGCTTGGTCCAGCGCAGCA
CCAGCTGGGCCCAGACGAACTCGGTCGCCCAGATCGCCATGCCGCCGAAGATCACCAGCCAGCCGGGGC
CCGGCAGCACCAGCATGAGCACACCCGCGATCACCACGCCGAGACCGACGATGAAGACACCGACCTGCC
AGCTCAGGTGGAGCGCCTTGGACGCCTTGATGAAACCCGGCGCCCGCGAGCCCAGCGCGCGTTCCTCCCG
GTCCGATTCCCCCGTGGCGGATACCGGGGACGCCTGCTCGGCGACCTTGCTCCGCTCGTCACTCTCCGCG
TTCATGAAGCTCAACTTACCCGACCTGTCTCCGTCACTGGAATGGGCGCATAACTCAAAGTTACACGCCG
CTGAGCGGGGGACCCGAAGCGTCACAAATGGGTCAGAGGGGTTTACAACGCCACCGTAGGTGGCATGTC
GATTTCGCCGACGTGCGAATCCCCGAGCGCACACTGAGCGAAAGGCCCTGGCGCTTATGAACACCACGG
TCAGCTGCGAGCTGCACCTGCGCCTCGTTGTGTCGAGCGAGTCCTCACTGCCTGTACCCGCGGGCCTGCG
GTATGACACGGCCGATCCCTATGCCGTGCACGCCACCTTCCACACCGGAGCGGAGGAGACGGTCGAATG
GGTATTCGCCCGCGACCTCCTTGCCGAGGGGCTGCACCGGCCCACCGGCACCGGAGACGTCCGCGTCTGG
CCATCTCGTAGTCACGGTCAAGGCGTCGTATGCATCGCCCTGAGCTCCCCAGAGGGAGAAGCCCTGCTCG
AAGCCCCGGCGCGGGCCCTGGAGTCGTTCCTGAAGAGGACCGACGCCGCGGTTCCGCCCGGCACCGAGC
ATCGTCACTTCGATCTCGACACGGAGCTCTCCCACATCCTGGCCGAGAGCTGAGCCAGGCAGAGAGCCGC
TCTACGCCGTCCGACTCGGGGCGACGGCGTCGTGCTGACAACCGCATAGGGCAGACACCGGCGCCGTCG
TCGCGGAATCCACCGCGACGACGGCGCCGGCGCGTTCCCCGCCGCGCCGCCGGAGGGGTCCGTTCCGCTC
TCCGCCGGGCCCGCACCGGGCCCGGCACCGGCCGGCCGAGCCAGTAGAGTCAGCCGCCATCGGCAGGCG
CCCGCCCGCCGGAAGGCCAGGGAGCGAAGCGTGCTGATCCCTCACGACACCCGGATCGCCCTCGACGCG
GTGGTCGATCTGGTGAACACCGCACCGGAGAGCGGAGCCGCGGGGACGACCCCGGCGACAGACACGC
GGGCGGCCCGAGGACGGTCTCCCCGACATCGCCGCGCTGTACGCCTTCGCGGAGCGCCATCTCATCAGC
GGGGTCGGCACCCTCGGCGAGAAGGACCTCGGCGCCGTGCGCGACGTCCGGGCCCGCTTCGCCGAGGTC
```

Contd..
TTCGCGGCGCCCGACGCCCGCGTCGCCGCCGACCTGGTCAACCGGCTCGTCGCGGCGGCCGGGACCACCC
CGCAGCTCACGGACCACGACGGCTACGACTGGCACGTGCACTACTTCGCCCCGGACGCCTCGATCGCCGA
CCATCTCGCGGCCGACTGCGGCATGGCGCTGGCCTTCATCATCGTGGCGGGCGAGCAGGAGCGGCTGCG
GCGCTGCGAGGCCCCGGACTGCGGGCACGCGTTCGTCGACCTGTCGCGCAACCGCTCCCGCCGCTACTGC
TCCAGCCGTACGTGCGGGAACCGGCTCCACGTCGCGGCGTACCGGGCCCGGCGCAAGGAAGCCGCGGGC
TGACGCCCGGCACGGTGGCGCGAGGCGTCACAGCACGAAGAGATCGTGCAGCGCGGCCATCAGCAGCAG
GCCCCCGATCACCGTCAGGAAGATCATCAGGGGCGGCTGGGAGAGCGCGAAAAGACAGCCGCGGGCCTC
TTCGGCGGGGGGTGCGGGGGCATCGCCCCGGGAAGTGTCCACCATCTCGGGGTGATCATGACGCACCGG
CGGCGGTGTTGGCGATCAACCGGCTTCATTCTCCCGGGAGTTCACCGTCCCGTGGCCATCGATATTCGCTC
CGGCGTACGGGGAGCCGTCAGACATTCGGACCGCCGCCCGGAACGCACGCCGGCGGGGCCGGCCGACGC
CTCGGACGCCGCGCTTCTCAGATGCCGTGCTTCTTGAGGATC

```
** Peak Report ***
KNO  TIME     AREA      HEIGHT     MK   IDNO   CONC       NAME
 1   1.742    1090524    630697    V             16.3090
 2   1.803    2759591   1055567    VE            41.2702
 3   1.931     841734    440026    V             12.5883
 4   1.989    1899444   1050304    SVE           28.4066
 5   2.146       1222      1166    T              0.0183
 6   2.827       1691      1181    V              0.0253
 7   7.053      56479     14295                   0.8447
 8  10.909       1014       280                   0.0152
 9  13.388      34942     11651                   0.5226
             ----------------------------------------------
             6686640    3205166                 100.0000
```

ESCHERICHIA COLI HAVING ACCESSION NO. PTA 1579 AND ITS USE TO PRODUCE POLYHYDROXYBUTYRATE

FIELD OF INVENTION

The present invention relates to the field of recombinant deoxyribonucleic acid (DNA) technology. Specifically, the invention relates to identification of the genes responsible for poly-beta-hydroxybutyrate biosynthesis pathway from *Streptomyces aureofaciens* NRRL 2209, creation of a plasmid vector carrying the said gene and expression of this gene in *Escherichia coli* designated as NCIM 5128 and bearing ATCC Accession No. PTA 1579, which is used for synthesis of polyhydroxybutyrate in recoverable amounts of at least 60% of dry bacterial cell mass.

BACKGROUND OF THE INVENTION

Lemoigne in 1926 discovered the presence of PHB (poly-beta-hydroxybutyrate) in Bacillus. This has been reported to be present in a multitude of other bacterial genera, including Azotobacter, Alcaligenes, Psuedonomas, Rhizobium, Chromatium, Acinetobacter, Rhodospirillum and some species of cyanobacteria. It is also reported to be present in certain actinomycetes in very minute quantities. PHB is synthesized and stored by these microorganisms essentially as an energy source under stress conditions. PHB, a homopolymer of D-(–)-3-hydroxybutyrate, has properties comparable to synthetic polymers like polypropylene. PHB is commercially produced by fermentation technology using *Alcaligenes eutrophus* (*Ralstonia eutropha*) and is marketed under the brand name Biopol. In the present global environment awareness, as against synthetic polymers which are persistent by nature, PHB is bestowed with the property of biodegradability. Besides being used in packaging industry, PHB has also been used as a source of chiral centers for the organic synthesis of certain antibiotics, in drug delivery and bone replacement applications. The biosynthesis of PHB has been studied extensively in *Alcaligenes eutrophus, Rhodospirullum rubrum*, Pseudomonas species and *Azotobacter beijerinckii*. β-ketothiolase, the first enzyme in the pathway and coded for by the phaA gene, first catalyzes the reversible condensation of two acetyl coenzyme A (CoA) molecules to acetoacetyl-CoA. Acetoacetyl-CoA is then reduced to D-(–)-3-hydroxybutyryl-CoA by NADPH dependent acetoacetyl-CoA reductase which is coded for by phaB gene. D-(–)-3-hydroxybutyryl-CoA monomer is then polymerized to PHB by PHB synthase coded for by the phaC gene. PHB in the bacterial cell accumulates as cytoplasmic inclusions when growth of the bacteria in culture is limited by a nutrient other than a carbon source. It may be oxygen deprivation, nitrogen deprivation, phosphate limitation, sulfate limitation and magnesium limitation. Once the limiting conditions are relaxed, PHB is metabolized down to preinduction levels. It has been shown that both β-ketothiolase and acetoacetyl CoA reductase activities increase in response to PHB-stimulating limitation conditions.

Some of the U.S. Patents covering production and extraction of PHB from microorganisms include the following: U.S. Pat. No. 4,786,598 to Lafferty et al. discloses a two-stage fermentation process where PHB is produced using *Alcaligenes latus*, U.S. Pat. No. 4,705,604 to Vanlautem et al. discloses using 1,2 dichloroethane to simultaneously remove water from the bacterial suspension by azeotropic distillation and extract PHB from the cells, U.S. Pat. No. 4,477,654 to Holmes et al discloses limiting the nitrogen nutrient source to microbiologically accumulate 3-hydroxybutyrate polymers, U.S. Pat. No. 4,433,053 discloses a fermenting process for PHB accumulation using *A. eutrophus* where a nutrient required for growth is limited, U.S. Pat. No. 4,336,334 to Powell et al. shows a microbiological process for producing PHB using *Methylobacterium organophilum*, U.S. Pat. No. 4,358,583 to Walker et al. discloses extracting PHB by first flocculating the cells by heat or pH treatment then extracting with a suitable solvent, U.S. Pat. No. 4,138,291 to Lafferty discloses bacterial strains assimilating various carbon sources and converting them to PHB, U.S. Pat. No. 5,518,907 to Dennis discloses Cloning and expression in *Escherichia coli* of the *Alcaligenes eutrophus* H16 poly-beta-hydroxybutyrate biosynthetic pathway, U.S. Pat. No. 5,798,235 to Peoples, et. al., gene encoding bacterial acetoacetyl Co-A reductase and U.S. Pat. No. 5,650,555 to Somerville et. al. discloses transgenic plants producing polyhydroxyalkanoates. U.S. Pat. No. 5,512,456 to Dennis discloses method for the improved production and recovery of poly-beta-hydroxybutyrate from transformed *Escherichia coli*, U.S. Pat. No. 5,250,430 discloses Polyhydroxyalkanoate polymerase from *Zoogloea ramigera*.

Among the prokaryotes, the actinomycetes constitute an important part of the microbial community responsible for the degradation and recycling of natural substrates. Accumulation of PHB has been reported from nine different strains of Streptomyces by Kannan and Rehacek (Formation of poly-beta-hydroxybutyrate by actinomycetes. Indian J. Biochem., 7:126–129, 1970). A possible role in thew biosynthesis of polyketide-derived phenolic metabolites such as actinorhodin or antimycin has been suggested by Kannan and Rehacek (Formation of poly-beta-hydroxybutyrate by actinomycetes. Indian J. Biochem., 7:126–129, 1970) and Packter and Flatman (Characterization of acetoacetyl-CoA reductase (3-oxoreductase) from *Streptomyces coelicolor*, its possible role in polyhydroxybutyrate biosynthesis. Biochem. Soc. Trans., 11:598–599, 1983). *Streptomyces aureofaciens* NRRL 2209 is a very poor accumulator of PHB and has been reported by Kannan and Rehacek (Formation of poly-beta-hydroxybutyrate by actinomycetes. Indian J. Biochem., 7:126–129, 1970) to accumulate PHB upto 1.10% of the dry cell mass. These bacteria are not as amenable as *Escherichia coil* to genetic manipulations and certainly are not as well characterized. *Escherichia coli* as a host cell has been exploited for producing molecules like the human growth hormone, insulin and interferon.

Thus, although polyhydroxybutyrate and other polyalkanoate biosynthesis genes have been isolated and characterized in various organisms such as *Ralstonia eutropha* (formerly known as *Alcaligenes entrophus*), there are several disadvantages in the use of these genes for production of polyalkanaoates on a large scale. For instance, when these genes are cloned into bacteria such as *E. coli*, the eventual production of alkanoate is not substantial. Further, there is no instance in the prior art wherein DNA fragments are isolated from actinomycetes and expressed in a heterogeneous host for production of polyhydroxybutyrate.

In order to make PHB production regulatable; a need exists for cloning of the PHB biosynthetic pathway from *Streptomyces aureofaciens* NRRL2209, its introduction and expression in *Escherichia coli*.

OBJECTS OF THE INVENTION

The main object of the invention is to provide a method for cloning of genes coding for poly-beta-hydroxybutyrate biosynthesis pathway from *Streptomyces aureofaciens* NRRL2209 and expression thereof in *Escherichia coli*.

Another object of the present invention is to identify the genomic sequences responsible for poly-beta-hydroxybutyrate biosynthesis pathway, from *Streptomyces aureofaciens* NRRL2209.

Yet another object of the present invention is to clone the genes responsible for poly-beta-hydroxybutyrate biosynthesis pathway, in a multicopy plasmid vector, thus creating a new vector which carries the nucleotide sequence responsible for the PHB synthesis pathway.

Yet another object of the present invention is to transform *Escherichia coli* with a multicopy plasmid vector for expression of the PHB biosynthesis pathway genes in the bacterial host.

Another object of the present invention is to produce PHB using transformed *Escherichia coli* in recoverable quantities.

SUMMARY OF THE INVENTION

Accordingly, the present invention provides a method for isolation of genes coding for poly-beta-hydroxybutyrate (PHB) biosynthesis pathway from *Streptomyces aureofaciens* NRRL2209, expressing the said genes in *Escherichia coli* and producing PHB using the transformed *Escherichia coli* to the extent of 60% or more of the cell weight.

DETAILED DESCRIPTION OF THE INVENTION

Accordingly, the present invention provides a method for the production of poly-beta hydroxybutyrate (PHB) using recombinant *Escherichia coli*, said method comprising the steps of:

i) isolating the DNA sequence coding for the poly-beta-hydroxybutyrate (PHB) biosynthetic pathway, from *Streptomyces aureofaciens* NRRL2209, ii) cloning the DNA sequence coding for PHB pathway into a plasmid vector pGEM-3Z to obtain a multicopy vector designated as pSa240, iii) transforming *Escherichia coli* JM109 with the plasmid vectyor pSa240 to obtain recombinant *Escherichia coli* JM109 bearing accession No. PTA1579 and harbouring the gene responsible for production of PHB, and iv) culturing recombinant *Escherichia coli* JM109 in a conventional medium containing glycerol and recovering poly-beta-hydroxybutyrate.

In an embodiment, the nucleic acid fragment coding for poly-beta-hydroxybutyrate synthesis pathway is a 4.826 Kb long fragment (SEQ ID NO: 1).

In another embodiment the nucleic acid fragment coding for PHB pathway is isolated from *Streptomyces aurefaciens* NRRL2209.

In yet another embodiment, the DNA sequence coding for PHB pathway is cloned into a multicopy plasmid vector named pGEM-3Z.

In another embodiment, the plasmid vector harbouring the gene coding for PHB pathway is pSa240.

In yet another embodiment, *Escherichia coli* JM109 is transformed with the multicopy plasmid vector pSa240 at a temperature in the range of 14°–18° C. in the presence of T4 DNA ligase enzyme.

In another embodiment, the recombinant *Escherichia coil* JM109 is deposited with the American Type Culture Collection, USA and has received accession No. PTA1579. The deposit is made in compliance with the Budapest Treaty requirements.

In yet another embodiment, the transformed recombinant *Escherichia coli* JM109 when cultured in medium containing glycerol expresses the said biosynthetic pathway gene by producing poly-beta-hydroxybutyrate in recoverable quantities of at least about 60% of the dry cell mass of the *Escherichia coli* JM109 bacterial host.

The *Escherichia coli* JM109 bacterial host has been deposited with ATCC and bears Accession Number PTA No. 1579.

The transformed and genetically modified strain *Escherichia coli* JM109 harbors the plasmid pSa240 expresses gene for ampicillin resistance and the polyhydroxybutyrate biosynthetic operon obtained from *Streptomyces aureofaciens* NRRL2209. The original *Escherichia coli* JM109 strain was procured from ATCC and bears accession number 53323.

As said earlier, polyhydroxybutyrate and other polyhydroxyalkanoate biosynthesis genes have been isolated, characterized and patented from organism like *Ralstonia eutropha* (formerly known as *Alcaligenes eutrophus*), *Rhodospirillum rubrum, Zoogloea ramigera*. The Applicants have now have isolated, cloned, sequenced and characterized a 4.826 kb Sau3A I restriction endonuclease fragment (SEQ ID NO: 1) from the genomic DNA of *Streptomyces aureofaciens* NRRL2209 and this fragment carries all the genetic information required for the synthesis of polyhydroxybutyrate upon it being used to transform *Escherichia coli* JM109. This is the first instance of its kind where DNA fragment isolated from a member of actinomycetes has been expressed in a heterologous host for the production of polyhydroxybutyrate. The transformed *Escherichia coli* harboring the 4.826 kb Sau3A I restriction endonuclease fragment preferentially uses glycerol as a carbon source for the synthesis of polyhydroxybutyrate. The putative polyhydroxybutyrate biosynthesis genes that the applicants have isolated does not show significant sequence similarity at amino acid level with any of the reported polyhydroxybutyrate biosynthesis gene sequences. While *Streptomyces aureofaciens* NRRL2209 accumulates only about 1% polyhydroxybutyrate, the DNA fragment that the applicants have isolated from this organism and introduced into *Escherichia coli* JM 109 supports production and accumulation of polyhydroxybutyrate to the extent of 60% of dry cell mass of this heterologous host. The novelty of the patent is the isolation, cloning, sequencing and heterologous statement of a 4.826 kb DNA sequence (SEQ ID NO: 1) from *Streptomyces aureofaciens* NRRL2209 for the production of polyhydroxybutyrate.

The novelty of the invention resides in isolation, cloning, sequencing and characterization of a 4.826 kb Sau3A I restriction fragment from the genomic DNA of *Streptomyces aureofaciens* NRRL 2209. The Sau3A I DNA fragment harbors genes responsible for the synthesis of polyhydroxybutyrate. This Sau3A I DNA fragment when cloned and introduced into *Escherichia coli* JM109 as plasmid vector pSa240 supports the synthesis of polyhydroxybutyrate to the extent of at least 60% dry mass of the bacterial cell. The recombinant *Escherichia coli* JM109 (ATCC PTA-1579) utilizes glycerol as a carbon source for the synthesis of polyhydroxybutyrate.

However, with the use of other carbon sources individually or in combination it may be possible to order the synthesis of the other homo- or co-polymers of hydroxyalkanoates.

To describe in detail, the present invention relates to a novel method for improved production and recovery of PHB using *Escherichia coli* JM109. The invention is described in detail by the accompanying drawings illustrated herein below and the following description and examples.

FIGS. 2a and 2b represent respectively the agarose gel electrophoresis of twenty four phaC positive clones and their Southern blot analysis using the 570 base pair Sac I DNA fragment spanning the central region of the phaC gene of *Ralstonia eutropha* as the probe.

FIG. 8 represents the nucleotide sequence of the 4.826 kilobase Sau3A I genomic DNA fragment from *Streptomyces aureofaciens* NRRL2209 cloned and present as an insert in the pSa240 plasmid (SEQ ID NO: 1).

Figure 1:
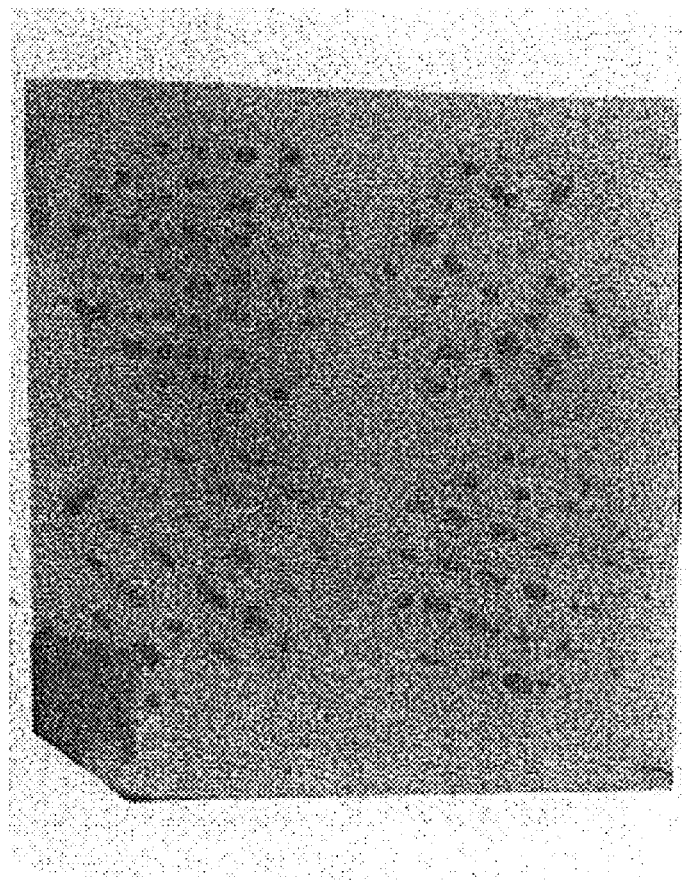
FIG. 1 represents colony hybridization of *Streptomyces aureofaciens* NRRL2209 Sau3A I subgenomic library with the 1.55 kilobase Nco I/Stu I restriction fragment of the phaC gene from *Ralstonia eutropha*.

In this invention, building a subgenomic library of *Streptomyces aureofaciens* NRRL2209 was commenced with the genomic DNA being partially digested with the restriction endonuclease Sau3A I, DNA fragments 2–6 kilobase in size isolated, purified and shot gun cloned by ligation to the BamH I restriction site of pGEM-3Z plasmid vector. The ligation mix was later used to transform *Escherichia coli* JM109 and develop a subgenomic library. The subgenomic library was screened for the presence of the phaC gene using the 1.55 kilobase Nco I/Stu I DNA fragment spanning the phaC gene from *Ralstonia eutropha* as the probe and using standard colony hybridization procedures. Twenty four clones which gave strong positive signal were isolated and the recombinant plasmid DNA was purified from each of them.

In another embodiment of the present invention the insert from the each of the recombinant plasmids was released by restriction digestion with EcoR I/Pst I. The samples were electrophoresed in an agarose gel and Southern hybridization was done using standard procedures. The 570 base pair Sac I DNA fragment spanning the central region of the phaC gene of *Ralstonia eutropha* was used as the probe. On the basis of strong hybridization signal and large insert size twelve clones were selected.

In yet another embodiment of the present invention the above said twelve phaC positive clones were further characterized for the presence of the phaC gene by sequentially first hybridization with the 300 base pair Nsp (7524) V/Nco I restriction fragment and later with the 430 base pair Sac I/Stu I restriction fragment both from the phaC gene of *Ralstonia eutropha*. The twelve phaC clones were further characterized for the presence of the phaA gene by standard hybridization procedures using the 1.0 kilobase Stu I DNA fragment spanning the phaA gene of *Ralstonia eutropha* as the hybridization probe. Three phaA positive clones which gave strong hybridization signal were selected.

In still another embodiment of the present invention the above three clones which gave positive hybridization signals for the phaC and the phaA genes were analyzed for PHB production. One *Escherichia coli* JM109 clone harboring the designated pSa240 plasmid was found to produce PHB in substantial and recoverable quantities, and is deposited with ATCC, U.S.A. and afforded accession number ATCC PTA 1579

In another embodiment of the present invention the insert in the pSa240 plasmid was mapped with restriction enzymes and found to be approximately 5.0 kilobase in size.

In yet another embodiment of the present invention the insert in the pSa240 plasmid was subjected to nucleotide sequence and found to be 4.826 kilobase in size.

Experiments have been conducted which include the isolation, cloning and sequencing of the PHB biosynthetic pathway from *Streptomyces aureofaciens* NRRL2209, and the production and accumulation of PHB in recombinant *Escherichia coli* to a high internal concentration. All chemicals used in the experiments were obtained from the Sigma Chemical Company, United States Biochemicals, New England Biolabs and Promega Corporation, all from the U.S.A and Amersham, U.K. Streptomyces aureofaciens NRRL 2209 was from National Regional Research Institute, Perioa, Ill., U.S.A. and *Escherichia coli* JM109 was obtained from the American Type Culture Collection (ATCC), Manassas, Va., U.S.A. Luria Bertani broth (LB) and antibiotics were prepared according to Sambrook et al (Molecular Cloning: a laboratory manual, $2^{nd}$ edition, Cold Spring Harbor Laboratory, New York, 1989). The pGEM-3Z plasmid vector was obtained from Promega Corporation, Madison, Wis., U.S.A.

A subgenomic library of *Streptomyces aureofaciens* NRRL2209 was constructed by inserting 2–6 kilobase Sau3A I digested genomic DNA fragments in pGEM-3Z plasmid vector, followed by transformation of *Escherichia coli* JM109. Total *Streptomyces aureofaciens* NRRL2209 genomic DNA was prepared by the protoplast lysis method described by Tripathi and Rawal (Simple and efficient protocol for isolation of high molecular weight DNA from *Streptomyces aureofaciens*. Biotechnol. Tech., 12:629–632, 1998). Basic cloning techniques were followed as enumerated by Sambrook et al (Molecular Cloning: a laboratory manual, $2^{nd}$ edition, Cold Spring Harbor Laboratory, New York, 1989). The genomic DNA was partially digested with the restriction endonuclease Sau3A I. The restriction digested DNA was electrophoresed in 1.0% agarose gel and DNA fragments in the 2–6 kilobase range were excised from the gel, and purified by phenol extraction and ethanol precipitation. The plasmid pGEM-3Z DNA was linearized by restriction digestion with the restriction endonuclease BamH I, and purified by phenol extraction and ethanol precipitation. The Sau3A I partially digested genomic DNA fragments and the BamH I digested plasmid were subjected to ligation overnight at 16° C. using T4 DNA ligase (Promega, U.S.A) as per manufacturers recommendations The ligated DNA was used to transform *Escherichia coli*

JM109. The bacteria were plated onto LB plates containing ampicillin. The resultant ampicillin resistant bacterial colonies were used as the subgenomic library. The subgenomic library was screened by colony hybridization using the 1.55 kilobase Nco I/Sac I DNA fragment from *Ralstonia eutropha* spanning the phaC gene (which codes for polyhydroxybutyrate synthase enzyme) as the hybridization probe (FIG. 1). The colony hybridization procedure was followed according to Sambrook et al. (Molecular Cloning: a laboratory manual, $2^{nd}$ edition, Cold Spring Harbor Laboratory, New York, 1989). Among the phaC positive colonies, twenty four positive clones were selected on the basis of strong hybridization signal.

Plasmid DNA was isolated from the twenty four phaC positive recombinant *Escherichia coli* JM109, restriction digested with EcoR I and Pst I to release the insert. The restriction digested DNA samples were electrophoresed on an agarose gel (FIG. 2a), blotted onto Hybond N$^+$ membrane (Amersham, U.K) and screened by Southern hybridization using the 570 base pair Sac I DNA fragment spanning the central region of the phaC gene from *Ralstonia eutropha* as the hybridization probe (FIG. 2b). Standard procedures were used for probe preparation and Southern hybridization as described by Sambrook et al. (Molecular Cloning: a laboratory manual, $2^{nd}$ edition, Cold Spring Harbor Laboratory, New York, 1989). The probe was made radioactive by random primer extension method using Megaprime DNA labeling kit from Amersham, U.K. Both the insert and the vector gave hybridization signal. On the basis of strong hybridization signal and large size of the insert twelve clones were further selected for analysis.

Figure 3:
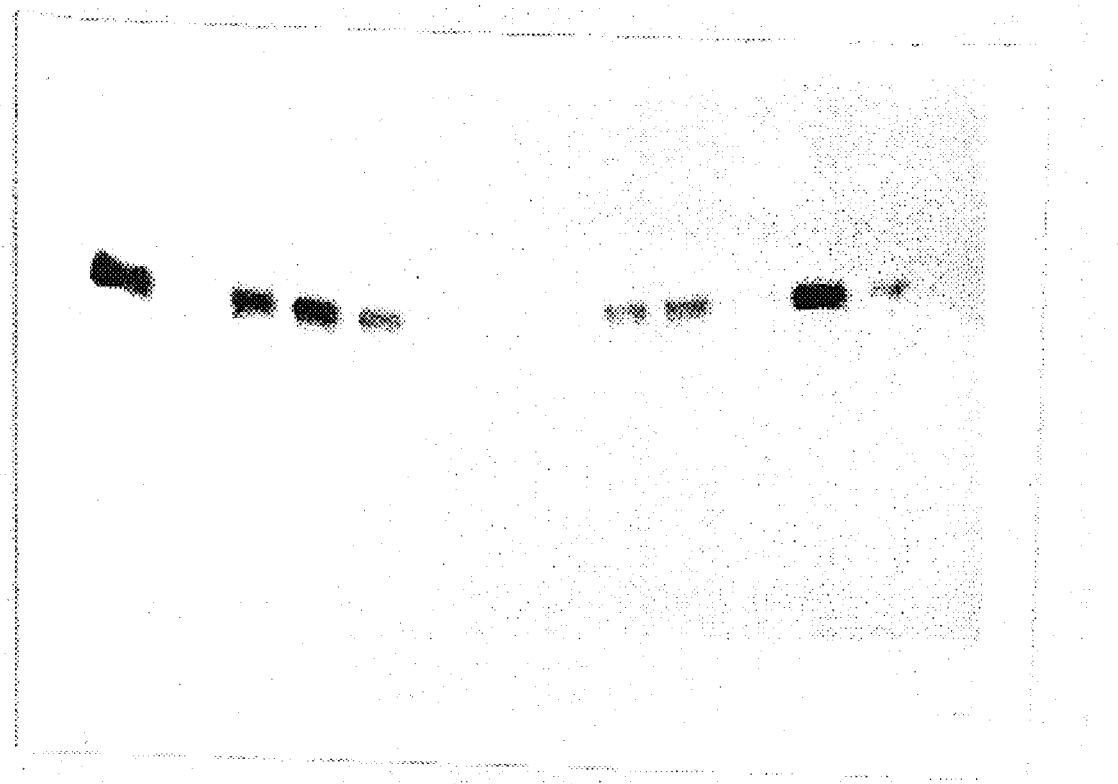
FIG. 3 represents the Southern blot analysis of twelve phaC positive clones hybridized to the 300 base pair Nsp (7524) V/Nco I restriction fragment spanning the 5' region of the phaC gene from *Ralstonia eutropha*.
Figure 4:
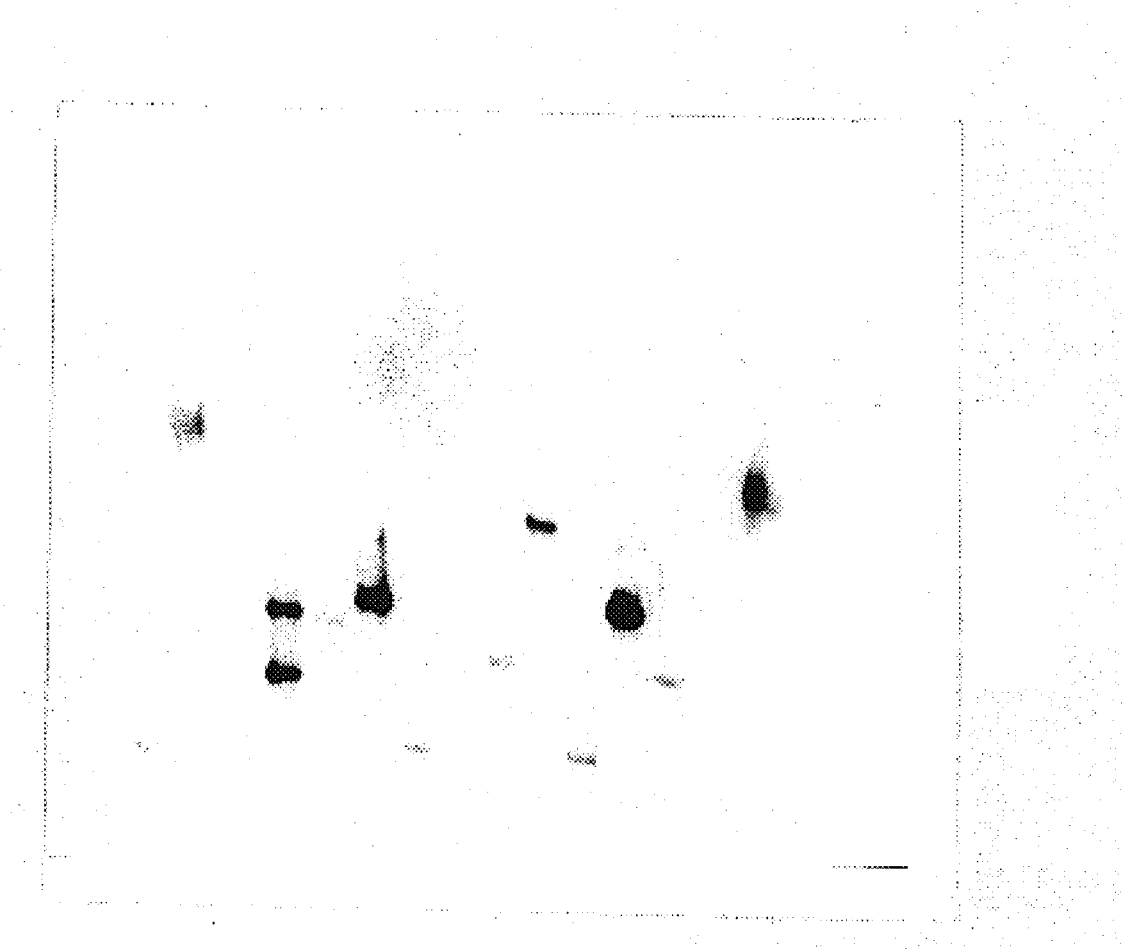
FIG. 4 represents the Southern blot analysis of the twelve phaC positive clones hybridized to the 430 base pair Sac I/Stu I restriction fragment spanning the 3' region of the phaC gene from *Ralstonia eutropha*.

In another experiment the plasmid DNA from the twelve selected clones was again restriction digested with EcoR I and Pst I, electrophoresed in 1% agarose gel, blotted onto Hybond N$^+$ membrane (Amersham, U.K) and subjected to Southern hybridization using the 300 base pair Nsp (7524) V/Nco I restriction fragment from *Ralstonia eutropha* which spans the 5' region of the phaC gene as the hybridization probe (FIG. 3). The probe was radioactive labeled by random primer extension method using Megaprime labeling kit of Amersham, U.K. No hybridization signal was seen from the insert of any of the twelve clones, however, the probe hybridized to the vector. The hybridization probe was stripped from the blot using standard methods and the blot was then rehybridized with the 430 base pair Sac I/Stu I DNA fragment spanning the 3' region of the phaC gene from *Ralstonia eutropha*. The probe was made radioactive by random primer extension method using Megaprime labeling kit of Amersham, U.K. While the inserts gave positive signal to the probe, the linearized vector gave very faint signal (FIG. 4).

Figure 5:
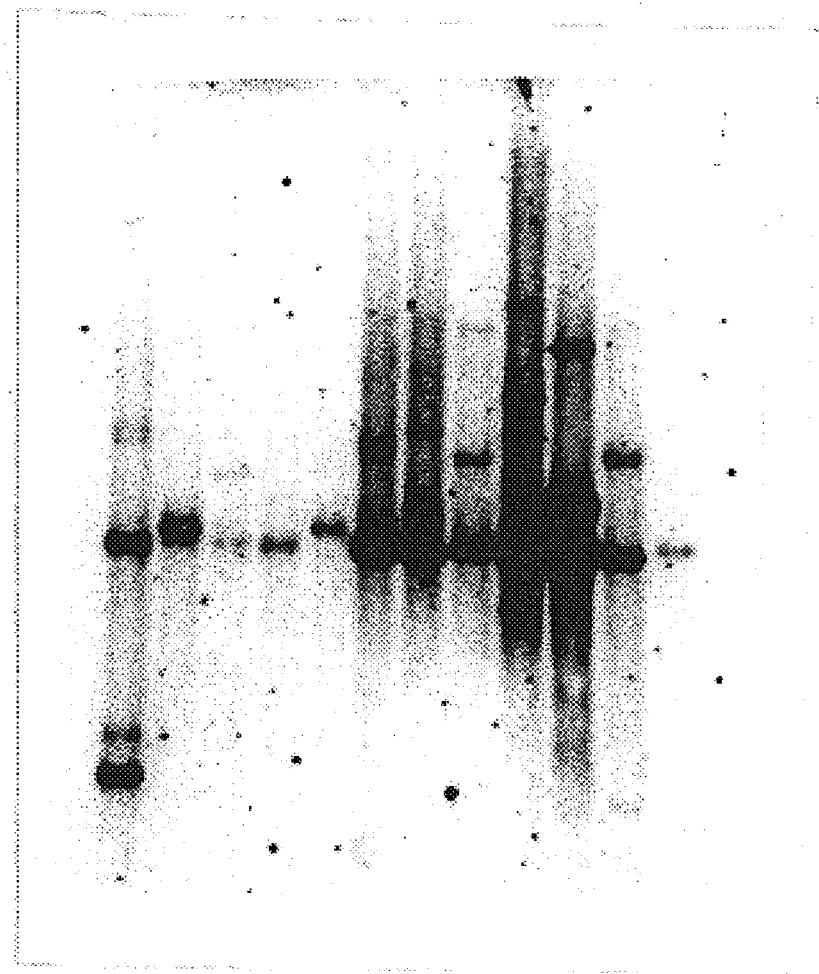
FIG. 5 represents the Southern blot analysis of the twelve phaa positive clones hybridized to the 1.0 kilobase Stu I restriction fragment spanning the phaA gene from *Ralstonia eutropha*.

In yet another experiment the plasmid DNA from the twelve selected clones was again restriction digested with EcoR I and Pst I, electrophoresed in 1% agarose gel, blotted onto Hybond N$^+$ membrane (Amersham, U.K) and subjected to Southern hybridization using the 1.0 kilobase Stu I DNA fragment spanning the phaa gene from *Ralstonia eutropha* as the probe. This gene codes for the enzyme β-ketothiolase. The probe was made radioactive by random primer extension method using Megaprime DNA labeling kit from Amersham, U.K. Inserts from all the clones gave varying degree of hybridization signals with this probe (FIG. 5). The linearized plasmid vector also gave hybridization signal.

Figure 6:
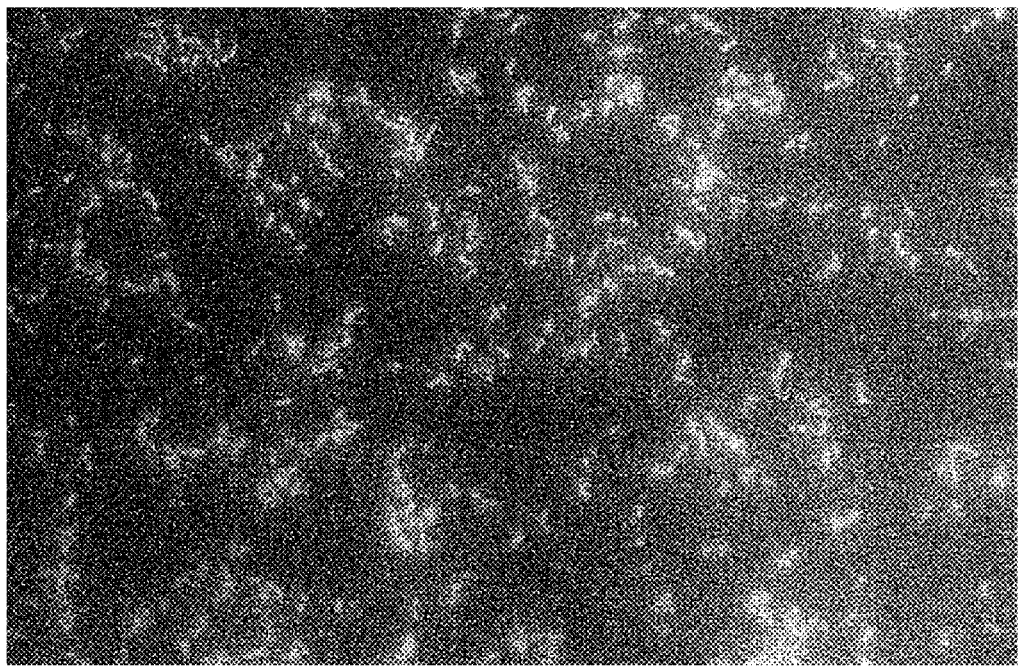
FIG. 6 represents the fluorescence photomicrographs of *Escherichia coil* JM109 harboring pSa240 showing orange fluorescence due to presence of intracellular PHB granules.

Based on the size of the insert and the strength of the hybridization signal of the recombinant clones, three clones designated pSa005, pSa067 and pSa240 were selected for further analysis. The individual recombinant *Escherichia coli* JM109 harboring the above said plasmids were grown in basal medium supplemented with ampicillin and 1% glycerol, stained with Nile blue A and observed for orange fluorescence at an excitation wavelength of 460 nm. No fluorescence was observed either in untransformed *Escherichia coli* JM109 or in recombinant *Escherichia coli* JM109 harboring pSa005 or pSa067 plasmid. *Escherichia coli* cells harboring the pSa240 plasmid, however, gave intense orange fluorescence (FIG. 6).

Figure 7:
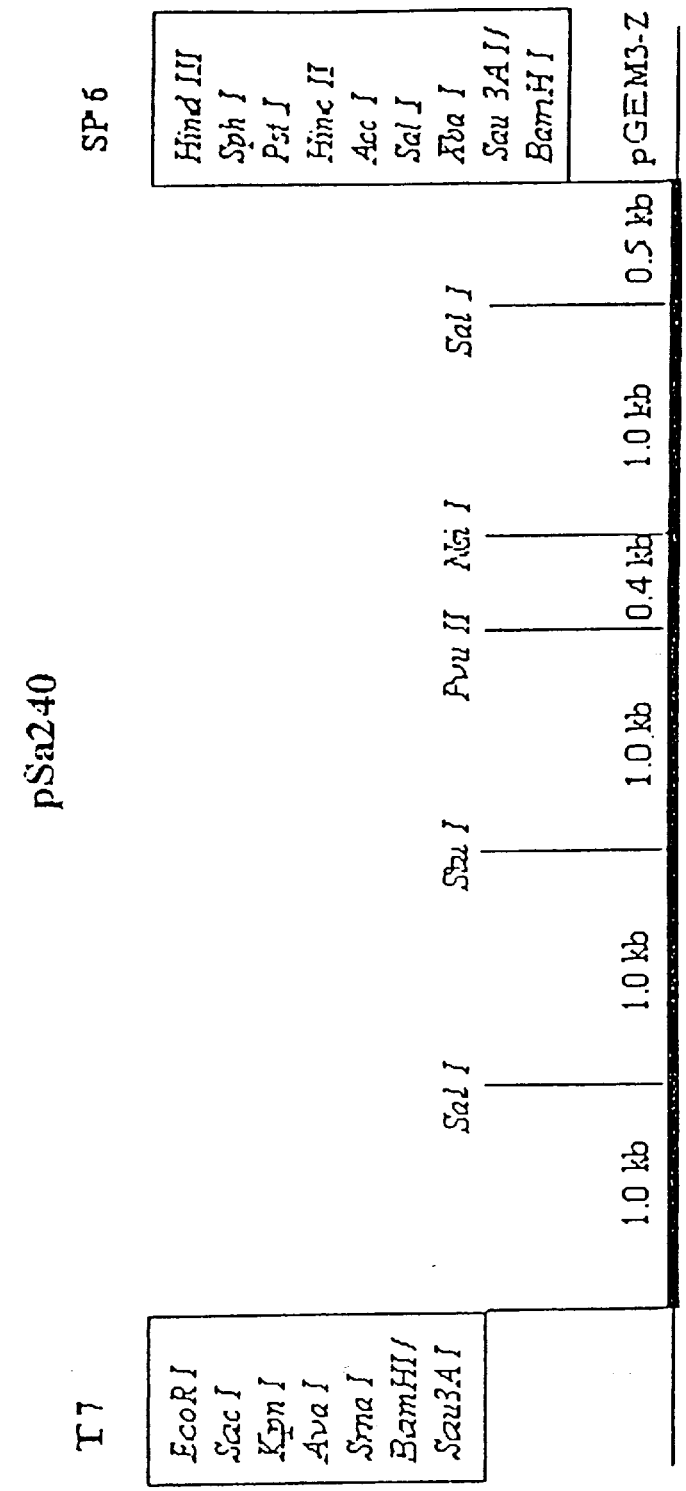
FIG. 7 represents the restriction endonuclease map of the pSa240 insert.

The pSa240 plasmid DNA was isolated from the recombinant *Escherichia coli* JM109 in large quantities using standard alkali lysis method (Sambrook et al. Molecular Cloning: a laboratory manual, $2^{nd}$ edition, Cold Spring Harbor Laboratory, New York, 1989). The insert cloned into the BamH I site of the pGEM-3Z plasmid vector was mapped with different restriction enzymes to: locate various restriction endonuclease sites within it, determine the size of different restriction fragments and to determine the total size of the insert in the pSa240 plasmid (FIG. 7). In this manner the total size of the insert DNA was found to be approximately 5.0 kilobase.

The approximate 5.0 kilobase DNA insert from *Streptomyces aureofaciens* NRRL 2209 in the pSa240 plasmid was bidirectionally sequenced by transposon insertion system. Transposons were randomly inserted using transposon insertion kit from Epicentre Technologies Corporation, U.S.A. DNA sequencing reactions were performed using ABI Prism BigDye Terminator Cycle Sequencing Kit from PE ABI, Connecticut, U.S.A. The size of the insert was found to be 4826 base pairs (FIG. 8).

Figure 9:
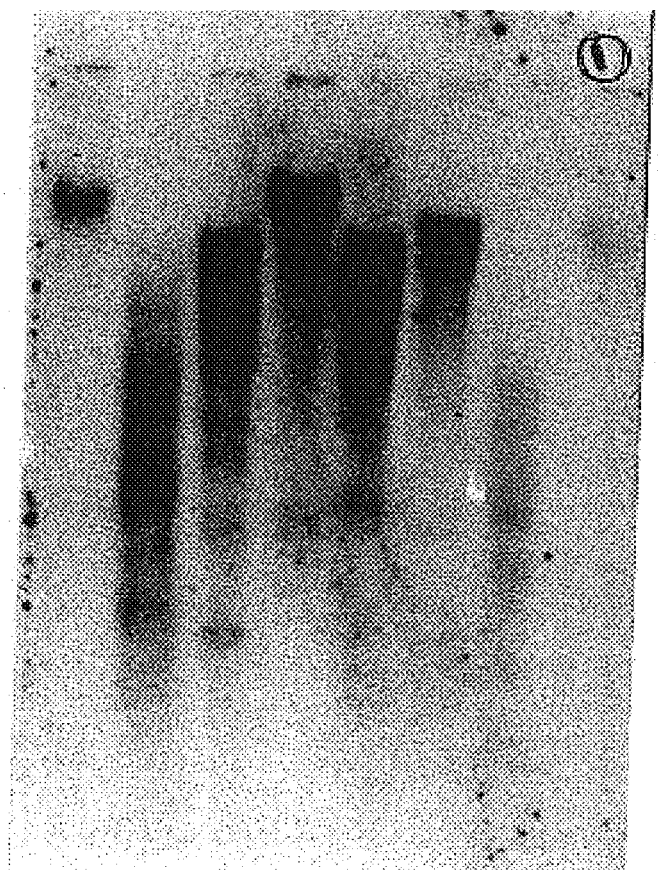
FIG. 9 represents Southern blot analysis of genomic DNA from *Streptomyces aureofaciens* NRRL2209 using the pSa240 insert as the hybridization probe.

Southern blot analysis by the method of Sambrook et al. (Molecular Cloning: a laboratory manual, $2^{nd}$ edition, Cold Spring Harbor Laboratory, New York, 1989) was performed to demonstrate presence of the PHB biosynthetic pathway in *Streptomyces aureofaciens* NRRL2209. The genomic DNA from the microorganism was extracted and digested with restriction endonucleases Apa I, Sal I, Sma I, BamH I and Nco I. The 4.826 kilobase insert released from pSa240 plasmid by restriction digestion with EcoR I and Pst I was gel purified, radioactive labeled and used as a probe. The PHB biosynthetic pathway is located on an approximate 20 kilobase DNA fragment flanked by BamH I and Nco I restriction endonuclease sites (FIG. 9).

Figure 10:
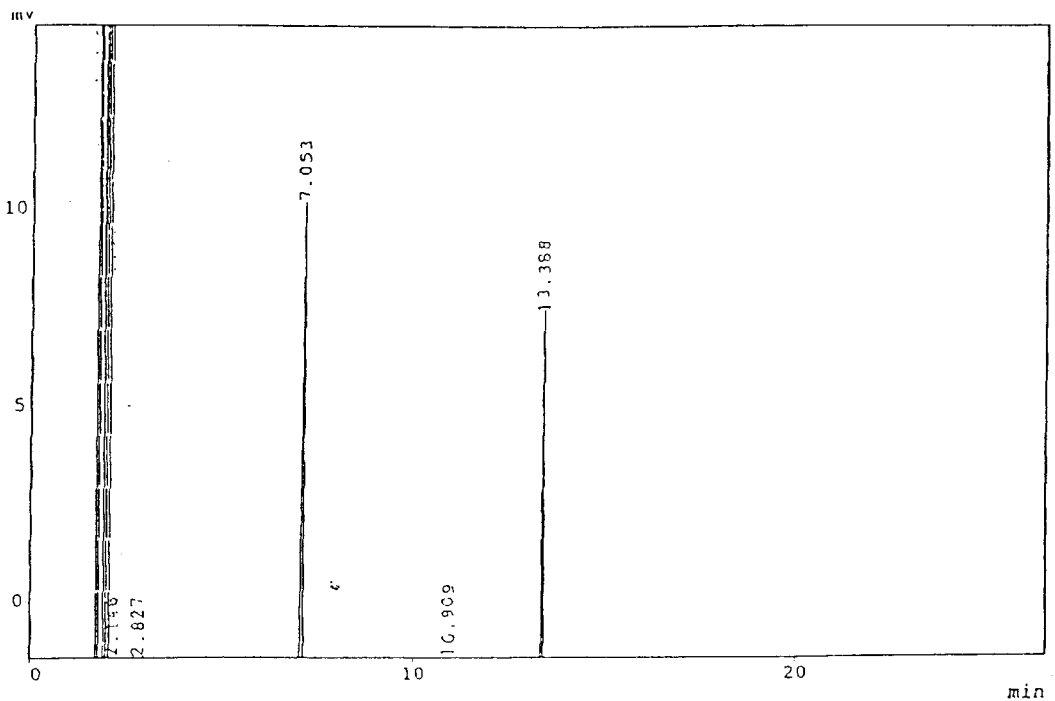
FIG. 10 represent the gas chromatogram of PHB extracted from *Escherichia coli* 109 harboring the pSa240 plasmid.

Twenty four hour cultures of *Escherichia coli* harboring the pSa240 plasmid insert were centrifuged to collect the cell mass. Total cell mass was esterified in presence of n-propanol, and subjected to gas chromatography (FIG. 10) to establish the presence of PHB in the recombinant *Escherichia coli* cells.

Figure 11:
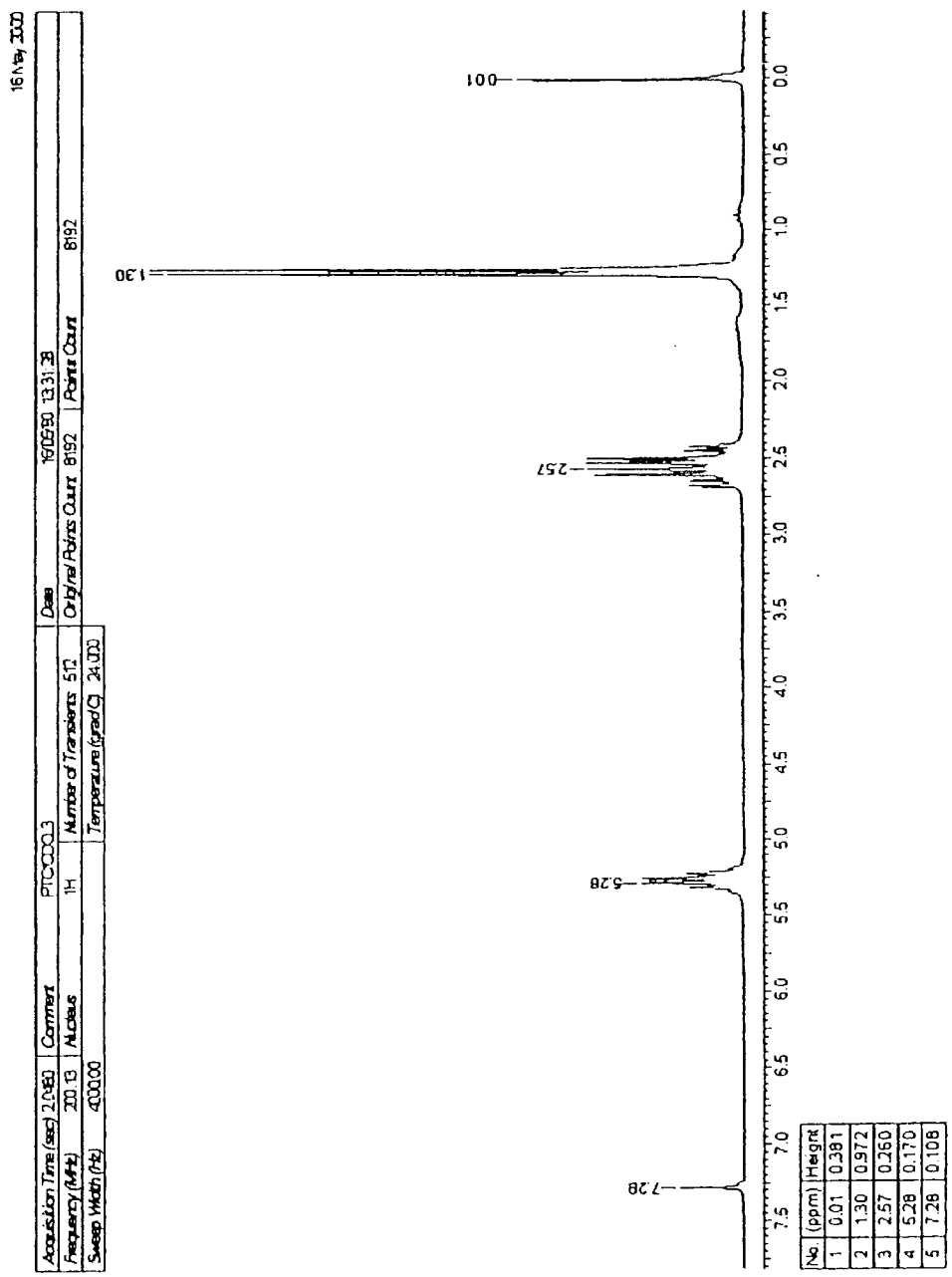
FIG. 11 represents nuclear magnetic resonance (NMR) spectrum of PHB isolated from *Escherichia coli* harboring pSa240 plasmid
Figure 12:
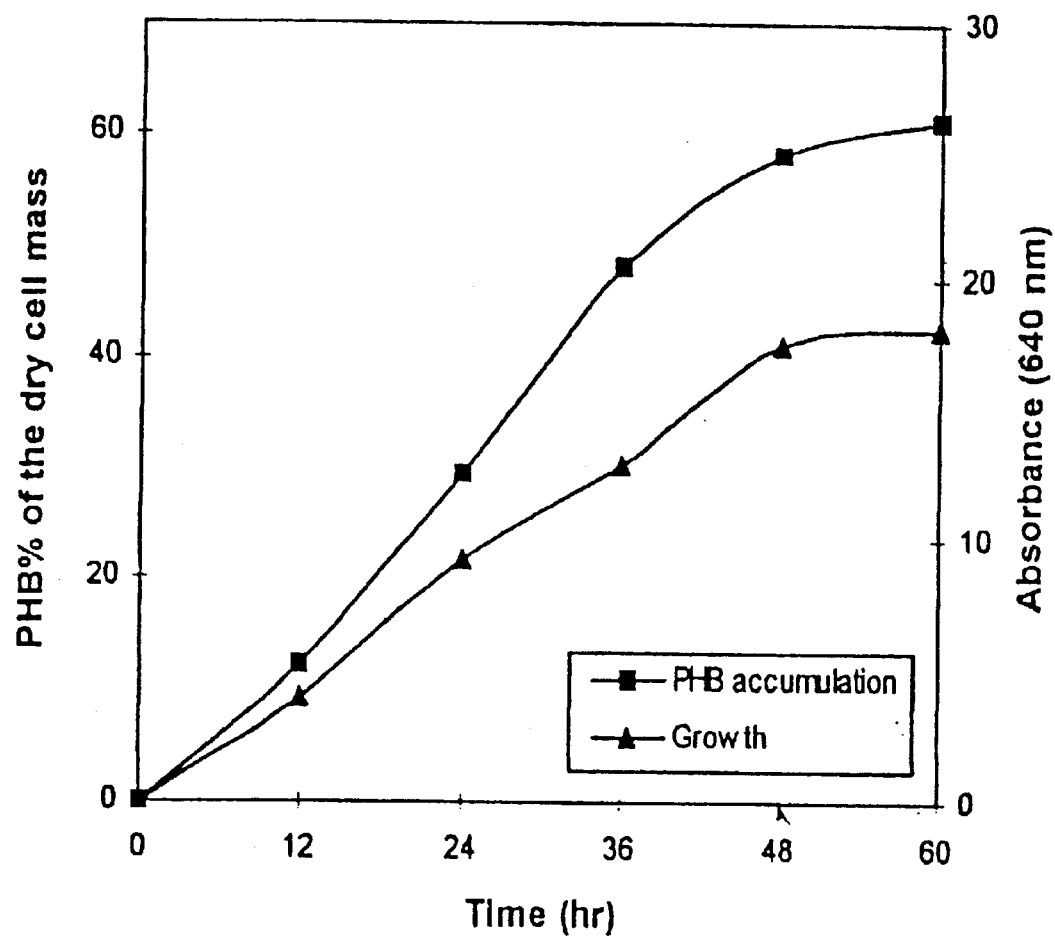
FIG. 12 represents a graph showing time course of growth and PHB accumulation by the recombinant *Escherichia coli* JM109 harboring the pSa240 plasmid and bearing accession number NCIM 5128 (ATCC PTA 1579).

PHB extracted from *Escherichia coli* harboring pSa240 plasmid was dissolved in deuteriated chloroform and analyzed by NMR (FIG. 11) which established the chemical identity of PHB. Experiments on PHB production revealed that *Escherichia coli* harboring the pSa240 plasmid clone produced intracellular PHB to substantial levels. These levels approached at least 60% of the bacterial cell dry weight in 48 hours of growth in culture. The high levels of expression obtained implies high transcriptional and/or translatinal activity in the recombinant *Escherichia coli*. PHB is produced by the *Escherichia coli* harboring the PHB pathway from *Streptomyces aureofaciens* NRRL2209 under non-induced conditions. Basal medium broth inoculated with *Escherichia coli* harboring the pSa240 plasmid and grown in presence of 1% glycerol as the sole carbon source accumulate PHB. PHB accumulation is higher in presence of glycerol rather than in presence of glucose, sucrose or molasses. The *Escherichia coli* strain harboring the pSa240 plasmid which carries a 4.826 kilobase PHB biosynthetic pathway from *Streptomyces aureofaciens* NRRL2209 which was produced according to the techniques described above has been deposited with the American Type Culture Collection, Manassas, Va., U.S.A. on Mar. 28, 2000 and bears accession number ATCC PTA 1579. The advantage of the smaller multicopy plasmid pSa240 is its ability to produce more copies per bacterial cell. While the invention has been described in terms of cloning the PHB biosynthetic pathway from *Streptomyces aureofaciens* NRRL2209 into *Escherichia coli* those skilled in the art of recombinant DNA technology will recognize that other microorganisms produce PHB and that the PHB biosynthetic pathway can be cloned into *Escherichia coli* in a manner contemplated within the spirit and scope of the appended claims.

The following examples are given by way of illustration and therefore should not be construed to limit the scope of the present invention.

EXAMPLE 1

The genomic DNA from *Streptomyces aureofaciens* NRRL2209 was incubated in presence of restriction endonuclease Sau3A I at 37° C. for 3 hours. The digested DNA was electrophoresed on 1% agarose gel and DNA fragments in the size range 2–6 kilobase were isolated and purified by process of phenolization and precipitation with ethanol.

EXAMPLE 2

The pGEM-3Z plasmid vector was restriction digested with the restriction endonuclease BamH I for 1 hour at 37° C. The linearized plasmid was obtained.

EXAMPLE 3

The linearized pGEM-3Z plasmid (example 2) and the 2–6 kilobase Sau3A I restriction fragments from *Streptomyces aureofaciens* NRRL2209 (example 1) were ligated at 16° C. with the help of T4 DNA ligase for 16 hours.

EXAMPLE 4

The ligation product (example 3) was used to transform *Escherichia coli* JM109 cells which were then plated onto LB plates containing ampicillin. Recombinant *Escherichia coli* JM109 colonies grew in presence of the antibiotic selection.

EXAMPLE 5

The recombinant *Escherichia coli* JM109 (example 4) colonies were blotted onto Hybond N$^+$ membrane (Amersham, U.K.). The master plates were stored under refrigeration.

EXAMPLE 6

The 1.55 kilobase Nco I/Sac I restriction fragment from *Ralstonia eutropha* spanning the phaC gene was purified and radioactive labeled using Megaprime DNA labeling kit (Amersham, U.K.), denatured by heating at 100° C. for 5 minutes and snap chilled on ice.

EXAMPLE 7

The Hybond N$^+$ membrane (example 5) was placed with the colony side up on a pad of absorbent paper soaked in denaturing solution (1.5 M NaCl, 0.5 M NAOH). After 7 minutes the blot was removed and placed in neutralizing buffer (3 M NaCl, 0.5 M Tris-HCl, pH 7.4). After 3 minutes the blot was washed in 2×SSC (0.3 M NaCl, 0.03 M sodium citrate, pH 7.0). The blot was transferred to dry filter paper, air dried, baked at 80° C. The blot was next prehyb ridized for 6–8 hours in hybridization buffer (1% crystalline BSA fraction V; 1.0 mM EDTA, pH 8.0:0.5 M Na$_2$HPO$_4$, pH 7.2; 7.0% SDS) at 60° C. in a hybridization incubator (Robin Scientific, U.S.A). The buffer was decanted off and fresh hybridization buffer was added along with the denatured radioactive labeled probe (example 6) and hybridization was carried out for 16–18 hours at 60° C. in a hybridization incubator (Robin Scientific, U.S.A). The buffer was decanted and multiple low stringency buffer (0.36 M NaCl; 0.02 M sodium phosphate, pH 7.7; 2 mM EDTA, pH 8) washes were given to the membrane at 60° C. for 15 minutes each. The membrane was then washed twice with high stringency buffer (36 mM NaCl; 2 mM sodium phosphate, pH 7.7; 0.2 mM EDTA, pH 8) at 62° C. for 15 minutes each. The membrane was next wrapped in cling wrap and exposed at –70° C. to X-ray film. The film was removed after two days and developed for the visualization of phaC positive hybridization signals.

EXAMPLE 8

Twenty four phaC positive *Escherichia coli* JM109 colonies (identified as in example 7) were taken from the master plates (example 6) grown over night in LB broth containing ampicillin and plasmid DNA was isolated from each one (Sambrook et al. Molecular Cloning: a laboratory manual, 2$^{nd}$ edition, Cold Spring Harbor Laboratory, New York, 1989).

EXAMPLE 9

The 570 base pair Sac I restriction fragment from *Ralstonia eutropha* spanning the central region of the phaC gene was purified and radioactive labeled using Megaprime DNA labeling kit (Amersham, U.K.), denatured by heating at 100° C. for 5 minutes and snap chilled on ice.

EXAMPLE 10

The plasmid DNA (example 8) was digested with restriction endonucleases EcoR I and Pst I for one hour. The digested samples were electrophoresed in 1% agarose gel. After electrophoresis the gel was rinsed with deionized water and placed in depurination solution (0.25 N HCl) for 20 minutes. The gel was again rinsed with deionized water and then placed in denaturation solution (example 7) for 45 minutes. The gel was again rinsed with deionized water and placed in neutralization solution (example 7) for 15 minutes. This step was repeated once. The gel was placed on HybondN$^+$ membrane (Amersham, U.K) and placed in a vacuum blotting unit (Pharmacia, Sweden). The transfer of DNA to the membrane was affected by application of vacuum and using 20×SSC buffer (3 M NaCl, 0.3 M sodium citrate, pH 7.0) for one hour as the elutant. The membrane was next separated from the gel, washed once with 2×SSC (example 7) and baked in an oven at 80° C. for 2 hours. The membrane blot was prehybridized and then hybridized (example 7) to the radioactive labeled 570 base pair Sac I fragment of the phaC gene from *Ralstonia eutropha*, (examle 9) and the blot was exposed to X-ray film at –70° C. The film was removed after two days and developed to visualize the positive hybridization signals.

EXAMPLE 11

The 300 base pair Nsp (7524) V/Nco I restriction fragment from *Ralstonia eutropha* spanning the 5' region of the phaC gene was purified and radioactive labeled using Megaprime DNA labeling kit (Amersham, U.K.), denatured by heating at 100° C. for 5 minutes and snap chilled on ice.

EXAMPLE 12

Out of the twenty four clones analyzed (example 10), twelve were selected on the basis of high molecular weight of the insert DNA and hybridization signal. Plasmid DNA from these clones was digested with restriction enzymes EcoR I and Pst I for one hour each. The restriction digested samples were electrophoresed, blotted onto HybondN+ membrane (Amersham, U.K) and hybridized (example 7) with the 300 base pair Nsp (7524) V/Nco I probe (example 11) and the blot was exposed to X-ray film at −70° C. for two days.

EXAMPLE 13

To strip off the 300 base pair Nsp (7524) V/Nco I probe, the membrane blot (example 12) was boiled in deionized water and left to stand in it for thirty minutes.

EXAMPLE 14

The 430 base pair Sac I/Stu I restriction fragment from *Ralstonia eutropha* spanning the 3' region of the phaC gene was purified and radioactive labeled using Megaprime DNA labeling kit (Amersham, U.K.), denatured by heating at 100° C. for 5 minutes and snap chilled on ice.

EXAMPLE 15

The membrane blot (example 13) was rehybridized (example 7) with the 430 base pair Sac I/Stu I probe (example 14) and exposed to X-ray film at −70° C. for two days.

EXAMPLE 16

The 1.0 kilobase Stu I restriction fragment from *Ralstonia eutropha* spanning the phaA gene was purified and radioactive labeled using Megaprime DNA labeling kit (Amersham, U.K.), denatured by heating at 100° C. for 5 minutes and snap chilled on ice.

EXAMPLE 17

The plasmid DNA from each of the twelve clones selected on the basis of high molecular weight of the insert DNA and hybridization signal (example 12) was digested with restriction enzymes EcoR I and Pst I for one hour. The restriction digested samples were electrophoresed, blotted onto HybondN+ membrane (Amersham, U.K) and hybridized (example 7) with the 1.0 kilo base Stu I probe (example 16) and exposed to X-ray film at −70° C. for two days.

EXAMPLE 18

Three clones which gave strong hybridization signals (examples 10, 15, 16) were selected and the *Escherichia coli* JM109 harboring these plasmid clones were grown for 24 hours in basal medium supplemented with ampicillin and 1% glycerol. About 100 $\mu$l of the cells were smeared on a glass slide, heat fixed and stained with 1% aqueous solution of Nile Blue A at 55° C. for 10 minutes. The slides were washed with tap water and then with 8% aqueous acetic acid. The smear was covered with a cover slip and observed under a fluorescence microscope at an excitation wavelength of 460 nm. Only one clone designated pSa240 gave bright orange fluorescence suggesting presence of PHB granules in the bacterial cells.

EXAMPLE 19

The *Escherichia coli* JM109 harboring pSa240 plasmid vector was grown in basal medium broth with ampicillin and 1% glycerol (example 18), pelted by centrifugation at 4,000 rpm and resuspended in 5 ml of methanol. The cells were again pelleted by centrifugation and vacuum dried. The dried cells were transferred to a tightly sealable glass tube for esterification. A 2 ml volume of 1,2-dichloroethane, 2 ml n-propanol containing hydrochloric acid (1 volume concentrated hydrochloric acid+4 volumes n-propanol) and 200 $\mu$l of internal standard (2.0 g benzoic acid in 50 ml n-propanol) were mixed and incubated for 4 hours in a water bath at 85 oC. The mixture was cooled, transferred to centrifuge tubes and centrifuged at 12,000 rpm for 15 minutes. 0.2 $\mu$l of the supernatant was injected into a gas chromatograph and PHB in the esterefied cell mass was detected by flame ionization detector.

EXAMPLE 20

The *Escherichia coli* JM109 harboring pSa240 plasmid vector was grown in LB broth with ampicillin and 1% glycerol (example 18), pelted by centrifugation at 4,000 rpm and resuspended in 5 ml of methanol. The cells were pelleted again by centrifugation and vacuum dried. The dried cells were dispersed in a 1:1 mixture of sodium hypochlorite (0.15% aqueous solution) and chloroform. The cell dispersion was kept on a shaker for 1.5 hours at 37° C. The dispersion was centrifuged at 10,000 rpm for 10 minutes. The heavy chloroform phase containing solubilized PHB was recovered and PHB precipitated by addition of five volumes of methanol. The precipitate was recovered by filtration and air dried.

EXAMPLE 21

The air dried PHB recovered from recombinant *Escherichia coli* JM109 cells harboring the pSa240 plasmid (example 20) was dissolved in deuteriated chloroform and analyzed by nuclear magnetic resonance to establish the chemical identity of PHB.

The Main Advantages of the Present Invention Are:

1. The newly identified 4826 base pair Sau3A I restriction fragment from the genomic DNA of *Streptomyces aureofaciens* NRRL2209 which carries the genes for PHB synthesis is isolated and cloned.

2. The newly identified 4826 base pair Sau3A I restriction fragment from the genomic DNA of *Streptomyces aureofaciens* NRRL2209 is cloned in a multicopy plasmid vector to create a new plasmid vector pSa240 which carries the nucleotide sequence of the PHB biosynthesis genes.

3. *Escherichia coli* JM109 when transformed with the pSa240 plasmid vector produces polyhydroxybutyrate (PHB) in recoverable quantities of at least 60% of cell dry mass utilizing glycerol as the carbon source.

What is claimed is:

1. A genetically modified *Escherichia coli* JM109 microorganism, capable of producing poly-beta-hydroxybutyrate in recoverable quantities of at least about 60% (w/w) of the genetically modified *Eschericia coli* JM109 dry cell mass and corresponding to deposit number ATCC PTA 1579.

2. A microorganism according to claim 1, wherein the microorganism is transformed by a multicopy plasmid vector comprising the nucleic acid sequence of SEQ ID NO:1.

3. A microorganism according to claim 2, wherein the plasmid vector is pSa240.

4. A microorganism according to claim 2, wherein the nucleic acid sequence of SEQ ID NO: 1 is a 4.826 kb fragment.

5. A multicopy plasmid vector pSa240 comprising the nucleic acid sequence of SEQ ID NO: 1.

6. A genetically modified *Escherichia coli* JM109, capable of producing poly-beta-hydroxybutyrate in recoverable quantities of at least about 60% (w/w) of the genetically modified *Eschericia coli* JM109 dry cell mass, and comprising the nucleic acid sequence of SEQ ID NO: 1.

7. A microorganism having or corresponding to deposit number ATCC PTA 1579.

8. An isolated nucleic acid having the sequence of SEQ ID NO: 1.

* * * * *

SEQUENCE LISTING

<160> NUMBER OF SEQ ID NOS: 1

<210> SEQ ID NO 1
<211> LENGTH: 4826
<212> TYPE: DNA
<213> ORGANISM: Streptomyces aureofaciens

<400> SEQUENCE: 1

| | | | | | |
|---|---|---|---|---|---|
| gatcggcggc | cggtcggcgg | tgctggccgc | ggtgaccctg | ggggcgctgg | ccgctccggc | 60 |
| ggtgctgctg | cgccggggc | tggcggccac | cgcggaggcg | ctggcggcgc | tggccctggt | 120 |
| gctgacgctg | ctggacgtgt | acgcggtcca | cgcggtggcc | gcgccggaca | ccgacggact | 180 |
| cggcttcacg | gccctcgcgt | cggcggtgct | cgcggcgctg | tggacggcgt | acgggctggc | 240 |
| gctgggcaag | ctgcgcctgc | cgttgccggc | cgccgtggtg | ctggcccagt | ggccgctgct | 300 |
| gttctgggcc | tggccgtgg | gcgcaccggc | gccggtggtc | gggtgggcgc | tgctggccac | 360 |
| cgcggtgctg | gacggggcga | tcgccctgtg | gggcaagggc | gccggggtgc | gggtcacggc | 420 |
| gtgcgtcggt | ggagcggtga | tgggcttctc | ggccctgatg | gtgggcctgg | cgctgtccct | 480 |
| gacggccccg | gggccgctcg | gggcggtggc | tccgggcgtg | ctgctgctga | cggcctcggc | 540 |
| ggcggccgtg | gccggggcgt | ggcgcgcgcc | gaagggtttc | gcgcggacgg | gtggtgcggt | 600 |
| ggcggggctc | gcggcggtgg | cggccgtcgg | cggcgtaccg | gcggcggcgc | tcccggcggg | 660 |
| ctggcgggtg | ctcgcgtacc | tgctgtgcgg | tctcgcgttg | acggcggtcg | tccgttcccg | 720 |
| gctgccgggc | cacgccgcgc | gcgggtact | ggcggcgtcg | ggggcggtgg | tggccggcgc | 780 |
| gctggtgtgg | gcgctgccgc | cgctcgcggc | ggtgctgctg | gggccggtga | cggtgctgtc | 840 |
| ggacgtgtgg | gcggggacgc | cggacggctt | ccggtccgcg | ctggggtcga | cgctgccctg | 900 |
| gtcggagctg | gccgcggccc | cggtggtgct | cgcgctggtg | gccgggcatg | ctggggcga | 960 |
| gcgtaaccgg | aggtggccgt | cggtcgtccg | gctccggcgc | cgttggccgg | tccttctggc | 1020 |
| tcgacgccgg | cccccggca | gcaccggcag | cgggagcccc | gggcacggat | gcgccgggcg | 1080 |
| cggccggggg | cgctgcgccg | tggcccggct | ggtccggctg | gtccggccgg | cccggtgcgg | 1140 |
| gggccggtgg | tcgcgggcgg | ccttccgcgc | cgacgctgcg | cggggtcgtc | ggcgcgggcg | 1200 |
| cggtggcgct | cggctggggg | gccctcctgc | tggccggcgc | gctgctggac | gtgccccacg | 1260 |
| cgctcgcgct | ggccggggag | acggctctgg | tgggcgtcct | gctcgccctg | gcggtccggg | 1320 |
| gtggcggcgc | cgagcggggc | gcgacggcga | tgccggtgac | cgctctggtg | gcttcggtgg | 1380 |
| ccggggcggt | gagcgccggg | ctgctgtcgc | tggcgtccga | ggggcctcg | tacgcggtgt | 1440 |
| tcggcgcgct | ggcggcgctg | ttcgccgggg | ccgctctgcg | ggcgggcgcc | gggtgccgc | 1500 |
| gtgcggtgtt | cgcggtcgcc | gcggtggtct | ggggcaccgt | gatcacgggg | ttggcgggcc | 1560 |
| ggtccctggg | gctcgccccg | cacgaggcg | ccccgctgat | gctgctggtg | ccggcgctga | 1620 |
| cggtgctgct | cggggcacga | ctgcggcgga | acccggtggc | cttgcccgtg | agctgacgg | 1680 |
| gagcgctggg | cgcgctcgtc | gccgtggggc | tcgcggtgtc | cgacgcgccg | ttcttggccc | 1740 |
| tggtgctggc | gctgtgcggg | gtgctggcgg | cggggacggc | ggtgcggccg | gagcggcggc | 1800 |
| cggtggcggg | ctacctggcg | cgacgctgt | tcgtgctggc | cacgtgggtg | cggctggcgg | 1860 |
| cctcggaggt | gtcgttcccg | gaggcgtaca | cgctgccggt | gacggtgccc | gcgctgctgg | 1920 |
| tcggtgcggc | gcggcggcgc | cgggaccggg | aggcctcgtc | gtggacgcg | tacgggccgg | 1980 |
| ggctcgcggc | gacgctgctg | cccagcctgg | cggtcgcctg | gaccgacccg | gactggctca | 2040 |

```
ggccgttgct gctggggacg gcggcgctgg tgatcaccct gctcggcgcg cgccaccggc    2100
tccaggcgct gctgctgctc ggcgggacgg tgctggcact ggtcggcctg cacgagctgg    2160
cgccgtacgt ggtgcaggtc gcgggtgcgc tcccccgctg gctcccgccc gccctggccg    2220
ggctgttgtt gctggtggtc ggagcgacgt acgagcagcg gctgcgggac gcccgccgtc    2280
tgaaggacgc gctggggcgg atgcggtgag ccgtgcccgg tccggggggcg cgcaggtcac    2340 ggcgtccccg ggccgggcgc cagtggcgtg ggcaacgcag agggcccggc cctctgtccg    2400
ggtgggcgat actgggttcg aaccagtgac ctcttcggtg tgaacgaagc gctctcccac    2460
tgagctaatc gcccgggcgc accgcaaaca ttaccccatg tcagcggtgc tcccggaccg    2520
tccccgggct actcgctgat cttccacggc atggtgagcc cgaacttcca gacgtagatc    2580
ccggccagca ccgccatgat cacgagcccg agcgtggtga ggatgatgtt gcgccgccgg    2640
accttgggat cgagggcccg ctgcgccgct tcggtgacct tgcgcttggt ccagcgcagc    2700
accagctggg cccagacgaa ctcggtcgcc cagatcgcca tgccgccgaa gatcaccagc    2760
cagccggggc ccggcagcac cagcatgagc acacccgcga tcaccacgcc gagaccgacg    2820
atgaagacac cgacctgcca gctcaggtgg agcgccttgg acgccttgat gaaacccggc    2880
gcccgcgagc ccagcgcgcg ttcctcccgg tccgattccc ccgtggcgga taccggggac    2940
gcctgctcgg cgaccttgct ccgtcgtca ctctccgcgt tcatgaagct caacttaccc    3000
gacctgtctc cgtcactgga atgggcgcat aactcaaagt tacacgccgc tgagcggggg    3060
acccgaagcg tcacaaatgg gtcagagggg tttacaacgc caccgtaggt ggcatgtcga    3120
tttcgccgac gtgcgaatcc ccgagcgcac actgagcgaa aggccctggc gcttatgaac    3180
accacggtca gctgcgagct gcacctgcgc ctcgttgtgt cgagcgagtc ctcactgcct    3240
gtacccgcgg gcctgcggta tgacacggcc gatccctatg ccgtgcacgc caccttccac    3300
accggagcgg aggagacggt cgaatgggta ttcgcccgcg acctccttgc cgaggggctg    3360
caccggccca ccggcaccgg agacgtccgc gtctggccat ctcgtagtca cggtcaaggc    3420
gtcgtatgca tcgcccctgag ctccccagag ggagaagccc tgctcgaagc ccggcgcgg    3480 gccctggagt cgttcctgaa gaggaccgac gccgcggttc cgcccggcac cgagcatcgt    3540
cacttcgatc tcgacacgga gctctcccac atcctggccg agagctgagc caggcagaga    3600
gccgctctac gccgtccgac tcggggcgac ggcgtcgtgc tgacaaccgc atagggcaga    3660
caccggcgcc gtcgtcgcgg aatccaccgc gacgacggcg ccggcgcgtt ccccgccgcg    3720
ccgccggagg ggtccgttcc gctctccgcc gggcccgcac cgggcccggc accggccggc    3780
cgagccagta gagtcagccg ccatcggcag gcgcccgccc gccggaaggc cagggagcga    3840
agcgtgctga tccctcacga cacccggatc gccctcgacg cggtggtcga tctggtgaac    3900
accgcaccgg agagcgagcc gccggggggac gaccccggcg acagacacgc gggcgggccc    3960
gaggacggtc tccccgacat cgccgcgctg tacgccttcg cggagcgcca tctcatcagc    4020
ggggtcggca ccctcggcga aaggacctc ggcgccgtgc gcgacgtccg ggcccgcttc    4080
gccgaggtct tcgcggcgcc cgacgcccgc gtcgccgccg acctggtcaa ccggctcgtc    4140
gcggcggccg ggaccacccc gcagctcacg gaccacgacg gctacgactg gcacgtgcac    4200
tacttcgccc cggacgcctc gatcgccgac catctcgcgg ccgactgcgg catggcgctg    4260
gccttcatca tcgtggcggg cgagcaggag cggctgcggc gctgcgaggc ccggactgc    4320 gggcacgcgt tcgtcgacct gtcgcgcaac cgctcccgcc gctactgctc cagccgtacg    4380
```

-continued

| | | | | | |
|---|---|---|---|---|---|
| tgcgggaacc | ggctccacgt | cgcggcgtac | cgggcccggc | gcaaggaagc | cgcgggctga | 4440 |
| cgcccggcac | ggtggcgcga | ggcgtcacag | cacgaagaga | tcgtgcagcg | cggccatcag | 4500 |
| cagcaggccc | ccgatcaccg | tcaggaagat | catcagggc | ggctgggaga | gcgcgaaaag | 4560 |
| acagccgcgg | gcctcttcgg | cgggggtgc | gggggcatcg | ccccgggaag | tgtccaccat | 4620 |
| ctcggggtga | tcatgacgca | ccggcggcgg | tgttggcgat | caaccggctt | cattctcccg | 4680 |
| ggagttcacc | gtcccgtggc | catcgatatt | cgctccggcg | tacggggagc | cgtcagacat | 4740 |
| tcggaccgcc | gcccggaacg | cacgccggcg | gggccggccg | acgcctcgga | cgccgcgctt | 4800 |
| ctcagatgcc | gtgcttcttg | aggatc | | | | 4826 |